United States Patent [19]

Okada et al.

[11] Patent Number: 4,941,870
[45] Date of Patent: Jul. 17, 1990

[54] METHOD FOR MANUFACTURING A SYNTHETIC VASCULAR PROSTHESIS

[75] Inventors: Masao Okada, Gifu; Kazuhiko Sakai, Kakamigahara; Haruo Kimura, Hashima; Yoshito Ikada, Uji, all of Japan

[73] Assignees: Ube-Nitto Kasei Co., Ltd., Tokyo; Research Development Corporation of Japan, Tokyo; Japan Medical Supply Co., Ltd., Hiroshima, all of Japan

[21] Appl. No.: 292,554

[22] Filed: Dec. 30, 1988

Related U.S. Application Data

[62] Division of Ser. No. 117,696, Nov. 6, 1987, Pat. No. 4,878,907.

[30] Foreign Application Priority Data

Nov. 10, 1986 [JP] Japan ................... 61-265578

[51] Int. Cl.$^5$ ............................. A61F 2/06
[52] U.S. Cl. ......................... 600/36; 427/2; 264/49; 264/344
[58] Field of Search ............ 623/1, 66; 600/36; 264/41, 49, 344, 561; 427/2

[56] References Cited

U.S. PATENT DOCUMENTS

| | | | |
|---|---|---|---|
| 4,459,252 | 7/1984 | MacGregor | 264/49 X |
| 4,657,544 | 4/1987 | Pinchuk | 623/1 |
| 4,704,130 | 11/1987 | Gilding et al. | 623/1 X |
| 4,725,273 | 2/1988 | Kira | 623/1 |
| 4,731,073 | 3/1988 | Robinson | 623/1 |
| 4,743,258 | 5/1988 | Ikada et al. | 623/1 |
| 4,759,757 | 7/1988 | Pinchuk | 623/1 |
| 4,813,966 | 3/1989 | Gilding et al. | 623/1 X |
| 4,822,352 | 4/1989 | Joh et al. | 623/1 |
| 4,834,746 | 5/1989 | Kira | 623/1 |
| 4,834,747 | 5/1989 | Gogolewski | 623/1 |
| 4,857,069 | 8/1989 | Kira | 623/1 |

Primary Examiner—Alan W. Cannon
Attorney, Agent, or Firm—Wenderoth, Lind & Ponack

[57] ABSTRACT

A synthetic vascular prosthesis comprises a hollow tubular base member having a multitude of continuous pores and formed of an elastomer material, and a hydrogel layer formed on the inner surface of the base member. The hydrogel layer is partly embedded in the inner portion of the base member at the pores, thereby permitting anchoring adhesion between the hydrogel layer and the base member. A method for manufacturing the synthetic vascular prosthesis is also disclosed, in which the formation of pores in the base member is effected by two separate steps and the hydrogel layer is formed after formation of an inner porous portion of the base member.

5 Claims, 1 Drawing Sheet

METHOD FOR MANUFACTURING A SYNTHETIC VASCULAR PROSTHESIS

This application is a division of Ser. No. 07/117,696 filed Nov. 6, 1987, U.S. Pat. No. 4,878,907.

BACKGROUND OF THE INVENTION

1. Field of the Invention

This invention relates to a synthetic vascular prosthesis having an antithrombogenic hydrogel layer on the inner surface of the prosthesis and also to a method for manufacturing such a prosthesis.

2. Description of the Prior Art

Synthetic vascular prostheses that are currently in practical use are all of the neointima formation type, so that after implantation into a living body, thrombi are immediately formed on the inner surface of the prosthesis. When the thrombi are developed to cover the inner walls of the synthetic vascular prostheses in a certain thickness, further thrombus is not formed, thus ensuring the flow of blood. Subsequently, the neointima grow whereby the synthetic vascular prosthesis acquires the antithrombogenic property, thus performing the function of a blood vessel. The synthetic vascular prosthesis of this type, however, has a disadvantage that it is not applicable to a small prosthesis having an inner diameter of about less than 4 mm. This is because the prosthesis is plugged by the thrombi prior to the formation of the neointimae, thus preventing an effective patency of the prosthesis.

On the other hand, research and development have recently been made on a synthetic vascular prosthesis of the type which has an antithrombogenic property by itself and thus does not need the formation of the neointima. These synthetic vascular prostheses are generally divided into two kinds. In one kind, a living body-derived anticoagulant such as heparin, urokinase or the like is impregnated in, or is fixed through covalent bonds or ionic bonds to, a synthetic vascular prosthesis substrate so as to impart the antithrombogenic property thereto. In the other kind, a hydrogel layer is formed on the inner surface of a synthetic vascular prosthesis so as to prevent direct contact between a substrate of the prosthesis and proteinous and cellular components in the blood, thereby acquiring the antithrombogenic property. The prosthesis of this kind is disclosed in, for example, Japanese Patent Publication No. 60-242857.

In the former instance, however, the impregnated anticoagulant will flow away and be lost, or if fixed, the anticoagulant will gradually lose its activity and efficacy. Therefore, an everlasting antithrombogenic property cannot be obtained.

The latter kind where the hydrogel layer is formed on the inner surface of the synthetic vascular prosthesis, is believed to be more suitable since the antithrombogenic property can be maintained substantially permanently. Further, the synthetic vascular prosthesis of this kind is applicable to a small-diametered portion of the blood vessel as the neointimae need not be formed.

It is known that a hydrogel layer has a good antithrombogenic property and is formed by graft polymerization on the inner surface of a tubular base member which is made of elastomer, typically polyurethane. The base member should be porous in order to render the prosthesis flexible and to facilitate a joining operation of the synthetic vascular prosthesis to a natural vessel by suture. The porous base member, however, permits the hydrogel to impregnate therethrough, which is not desirable because it promotes calcification throughout the base member and reduces the flexibility of the prosthesis. It has thus been proposed to provide a thin, non-porous, dense layer between the inner surface of the base member and the hydrogel layer, so that the hydrogel may be prevented from infiltrating into the base member. However, fabrication of the hydrogel layer on such a dense layer requires complicated operations such as plasma treatment of the inner surface of the dense layer under vacuum to generate radicals, graft polymerization of a hydrophilic monomer (acrylamide or the like) on the inner surface, and removal of the resultant homopolymer not grafted. In addition, expensive apparatuses such as a vacuum pump, a high frequency generator and the like are necessary for the plasma treatment.

Furthermore, the provision of a dense layer increases the stiffness of the prosthesis and reduces the compliance. The compliance, of which measurement will be described later, is a value which indicates a variation in inner capacity of the prosthesis when an internal pressure is exerted thereon. A larger value results in a larger variation in the inner capacity when the internal pressure is constant. Generally, the compliance of the synthetic vascular prosthesis is small compared with that of a natural blood vessel. The difference in compliance between the synthetic vascular prosthesis and the natural vessel, tends to develop an aneurysm at the joint or in osculated portion or to break the prosthesis thereat.

Accordingly, an object of the present invention is to provide a synthetic vascular prosthesis which has a satisfactory strength and compliance as well as a good antithrombogenic property.

Another object of the invention is to provide a method for manufacturing a synthetic vascular prosthesis of the type set forth above by relatively simple operation.

SUMMARY OF THE INVENTION

According to the invention, there is provided a synthetic vascular prosthesis which comprises a hollow tubular base member having a multitude of continuous cells or pores and formed of an elastomer material, and a hydrogel layer formed on the inner surface of the base member. The outer portion of the hydrogel layer is partially embedded in the inner portion of the base member at the pores to thereby achieve anchoring adhesion between the hydrogel layer and the base member.

This synthetic vascular prosthesis can be fabricated according to the method of the invention which includes the steps of dissolving an elastomer material in a solvent, adding an inorganic salt to the solution and adjusting the viscosity of the solution, subjecting the solution to extrusion into a hollow tube, and cutting the tube to a predetermined length to form a tubular base member. After the solvent is removed from the base member which is in turn solidified, the inorganic salt in the inner portion of the base member is removed by dissolution with an acid to form a porous inner portion. A hydrogel material is subsequently coated on the inner surface of the base member so as to form a hydrogel layer on the base member, with the hydrogel material partially infiltrating into the pores of the porous inner portion. Thereafter, the inorganic salt in the outer portion of the base member is removed by dissolution with an acid, thereby forming a porous outer portion having continuous pores.

Other objects, features and advantages of the invention will be apparent from the following detailed description thereof when taken in conjunction with the accompanying drawings.

DETAILED DESCRIPTION OF THE INVENTION

Figure 1:
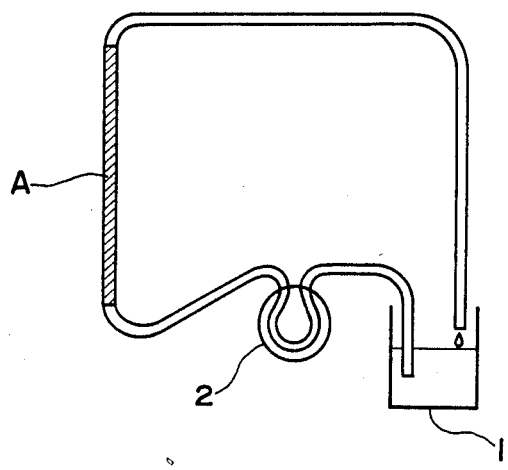
FIG. 1 is a schematic view for use in explanation of a step for forming a porous inner portion of a tubular base member according to the invention.

As described above, the synthetic vascular prosthesis of the invention includes a hollow tubular base member having a multitude of continuous pores and made of an elastomer, and a hydrogel layer formed on the inner surface of the tubular base member. The outer portion of the hydrogel layer is partially embedded in the inner portion of the base member at the pores thereof, thereby achieving an anchoring adhesion between the hydrogel layer and the base member.

The elastomers used above include, for example, polyurethanes, polyurethane ureas, their blends with silicone polymers, silicone polymers and other elastic polymers. In view of the durability in a living body, the polyurethanes or polyurethane ureas are preferably of the polyether type and are more preferably polyether-segmented polyurethanes or polyether-segmented polyurethane ureas.

The hydrogel layer is preferably made of polyvinyl alcohol having a degree of polymerization of from 500 to 10,000 and degree of saponification of not less than 80%, or ethylene-vinyl alcohol copolymers having a high content of vinyl alcohol. This is because these polymers are not dissolved in cold water and are likely to form a hydrogel, and they have a good antithrombogenic property and good durability.

When the hydrogel layer is partially embedded in the base member, the thickness of the embedded portion may be determined depending upon physical properties and porosity of the elastomer material from which the base member is made.

In accordance with the method of the invention, the synthetic vascular prosthesis is fabricated by the steps which comprise dissolving an elastomer material in solvent, adding an inorganic salt to the resultant solution and appropriately adjusting the viscosity of the solution to a desired level, extruding the solution into a hollow tube, and cutting the tube to a predetermined length to obtain a tubular base member. Thereafter, the solvent in the base member is removed and the base member is dried for solidification, and then the inorganic salt only in the inner portion of the base member is removed by dissolution with an acid to form an inner porous portion. A hydrogel layer is subsequently formed by coating a hydrogel material on the inner surface of the base member so that the hydrogel material is partly infiltrated into the pores in the inner porous portion. Finally, the remaining, outer portion of the base member is subjected to dissolution of the inorganic salt to form an outer porous portion having continuous pores.

The elastomer material used in this method may be selected from those mentioned before. The solvents particularly for the polyether-segmented polyurethanes or polyether-segmented polyurethane ureas include, for example, tetrahydrofuran, dimethylformamide, and the like.

The inorganic salts added to the solution of the elastomer material may be any salts which are capable of dissolving out with an acid such as hydrochloric acid, sulfuric acid, acetic acid and the like. Examples of the salts are calcium carbonate, magnesium oxide and magnesium hydroxide, and these salts may be used alone or in combination. In view of the formation of the continuous pores, the amount of the salts is preferably not less than 500 parts by weight per 100 parts by weight of the elastomer.

The extruder used for the extrusion process is favorably a screw extruder or a ram extruder having a circular die corresponding to the shape of the final product. Viscosity of the solution is so controlled as to adapt for the extrusion molding with these extruders by means of, for example, evaporation of the solvent.

The present invention is more particularly described below by way of example, in which a method of fabricating a synthetic vascular prosthesis is first described and then, the prosthesis per se is described.

EXAMPLE 100 parts by weight of polyether-segmented polyurethane were dissolved in 600 parts by weight of tetrahydrofuran to obtain a viscous polymer solution. 450 parts by weight of calcium carbonate having an average particle size of 1.7 micrometers and 90 parts by weight of magnesium oxide having an average particle size of 2 micrometers were added to the solution and kneaded, during which a part of the tetrahydrofuran was allowed to escape by vaporization. As a result, there was obtained a paste which had a viscosity of about 1.25 g/10 minutes when measured at room temperature by means of a melt indexer using a cylinder diameter of 9.55 mm, an orifice diameter of 2.096 mm and a load of 2160 g. The paste was supplied to a screw extruder and extruded from a circular die having an inner diameter of 3 mm and an outer diameter of 4 mm. While withdrawing with a takeup machine, the extruded product was cut into a length of about 50 to 60 cm to obtain a tubular base member A. The tubular base member was immersed in a water tank to remove the solvent for solidification, followed by sufficient drying.

In FIG. 1, there is shown a step of forming an inner porous portion B (FIG. 3) in the inner surface of the base member A. In this step, after the base member A was cut at opposite ends, 3N hydrochloric acid was supplied from a container 1 by means of a pump 2 and passed through the base member A for about 1 minute. As a result, the calcium carbonate and magnesium oxide which were present in the inner portion of the base member A, were removed by dissolution in the acid to form an about 20 micrometer thick inner porous portion B. Then, after the base member A was washed with water and dried, it was held upright with one end thereof being immersed in an aqueous solution of 5% polyvinyl alcohol having a degree of polymerization of 1700 and a degree of saponification of not less than 99%. The aqueous solution was then passed through the base member A by applying a suction force to the upper end thereof, and this sucking operation was repeated three times. The base member A was again dried, resulting in forming a hydrogel layer C (FIG. 3) having a total thickness of 25 to 30 micrometers a part of which, i.e. 15 to 20 micrometers thickness, was embedded in the inner porous portion B of the base member A.

Thereafter, the tubular base member A was entirely immersed in a sealed autoclave filled with 3N hydrochloric acid and the calcium carbonate and magnesium oxide present in the outside of the inner porous portion B were dissolved out under reduced pressure, thereby forming an outer porous portion D (FIG. 3) having continuous pores. After repetition of rinsing with dilute hydrochloric acid and washing with water, the base member was dried by a vacuum-freeze drying method at a reduced pressure of less than 2 mmHg for 12 hours in order to keep the porous condition.

Figure 3:
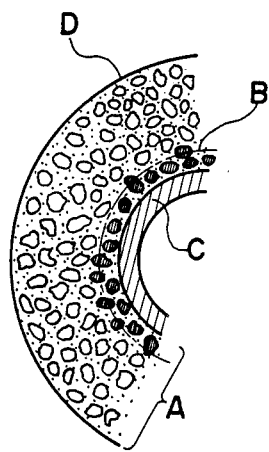
FIG. 3 is a schematic view showing one example of a synthetic vascular prosthesis according to the invention.

The synthetic vascular prosthesis having the hydrogel layer C obtained in this example had a section as shown in FIG. 3, with an inner diameter of about 3.00 mm and an outer diameter of 3.7 mm. The prosthesis had at the inside thereof the hydrogel layer C, which was composed of a smooth sub-layer with a thickness of about 10 micrometers on the base member A and an embedded sub-layer in the inner porous portion B of the base member A with a thickness of about 15 to 20 micrometers, thus a total thickness of the layer C being about 25 to 30 micrometers. The remaining portion of the prosthesis, i.e. the outer porous portion D, had a thickness of about 320 micrometers with an average pore size of 6 to 10 micrometers and porosity of about 80%.

The thus obtained synthetic vascular prosthesis of the invention felt somewhat rigid in a dry condition because the hydrogel layer was made of polyvinyl alcohol. However, when wetted sufficiently, the polyvinyl alcohol became softened as a hydrogel (hydrous gel), exhibiting a compliance and flexibility close to those of natural blood vessels.

The compliance and flexibility were measured according to the following methods.

Figure 2:
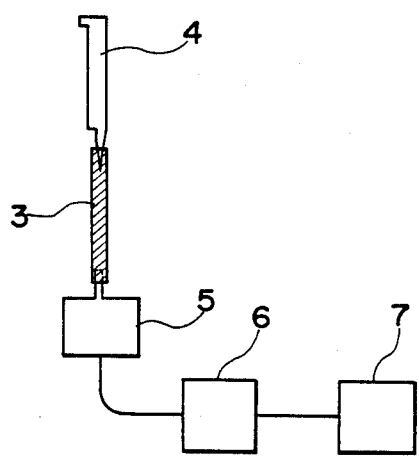
FIG. 2 is a schematic illustrative view showing how to measure compliance.

Measurement of Compliance:

The compliance is measured by a method shown in FIG. 2. A microsyringe dispenser 4 is used for supplying a predetermined amount of a physiological saline solution into a synthetic vascular prosthesis 3 every operation. The variation in inner pressure of the prosthesis 3 is detected with a pressure sensor 5 and recorded with a recorder 7 through an amplifier 6. The compliance of the prosthesis can be obtained according to the following equation (1) using the variation in inner pressure relative to the amount of the physiological saline solution injected into the prosthesis:

$$C = V/V_o \quad \text{-----(1)}$$

in which V is an increment of the inner volume of the prosthesis when the inner pressure increases from 50 mmHg to 150 mmHg, and $V_o$ is an inner volume of the prosthesis at an inner pressure of 50 mmHg.

Measurement of Flexibility:

The measurement of the flexibility was effected using the "Olsen" type flexibility measuring instrument.

When the modulus of elasticity in bending of a prosthesis is taken as E and the moment of inertia of the prosthesis is taken as I, the value EI can be obtained by the use of the Olsen type flexibility measuring instrument. This value was used as a standard for the flexibility.

The physical characteristics of the synthetic vascular prosthesis of the invention determined by these methods are shown in Table 1, along with a comparative synthetic vascular protheses which was provided with a polyether-segmented polyurethane inner layer (a dense layer) having a thickness of 50 micrometers between a base member and a hydrogel.

TABLE 1

|  | C (Compliance) | Flexibility (g · cm$^2$) |
| --- | --- | --- |
| Comparative Example | 0.056 | 2.0 |
| Example of the Invention | 0.164 | 1.1 |

As will be apparent from the foregoing, the synthetic vascular prosthesis according to the invention has a hydrogel layer having a good antithrombogenic property, which is embedded into pores of the inner porous portion of the base member, so that an intimate bonding between the hydrogel layer and the base member is ensured through anchoring adhesion. Since the hydrogel layer becomes softened in use, the compliance and flexibility of the prosthesis of the invention are close to those of natural blood vessels, remarkably reducing a danger of development of an aneurysm and a breakage of the prosthesis at a sutured portion. Further, the fact that the hydrogel layer is not embedded into the full thickness of the base member, prevents calcification and serves to maintain the flexibility of the prosthesis.

Moreover, the formation of pores in the base member according to the method of the invention is carried out in two stages, the first stage involving the formation of pores only in the inner portion of the base member. Subsequently, a hydrogel-forming material is coated on the inner portion. Thus, the formation of the pores and the coating can be carried out relatively simply.

Although the invention has been described with reference to the preferred embodiments thereof, many modifications and alterations may be made within the spirit of the invention.

What is claimed is:

1. A method for manufacturing a synthetic vascular prosthesis comprising the steps of:
   dissolving an elastomer material in a solvent;
   adding an inorganic salt to the solution and adjusting the viscosity of the solution;
   subjecting the solution to extrusion into a hollow tube;
   cutting said tube to a predetermined length to form a tubular base member;
   removing the solvent from said base member and drying said base member;
   removing the inorganic salt in the inner portion of said base member by dissolution with an acid to form a porous inner portion of said base member;
   coating a hydrogel material inside of said base member so that said hydrogel material, forms a hydrogel layer on said base member with partial infiltrating into the pores of said porous inner portion; and
   further removing the inorganic salt in the outer portion of said base member by dissolution with an acid, thereby forming a porous outer portion having a multitude of continuous pores.

2. A method according to claim 1, wherein said elastomer material is selected from the group consisting polyether-segmented polyurethanes and polyether-segmented polyurethane ureas.

3. A method according to claim 2, wherein said solvent is selected from the group consisting or tetrahydrofuran and dimethylformamide.

4. A method according to claim 1, wherein said inorganic salt is selected from the group of particles of calcium carbonate, magnesium oxide and magnesium hydroxide.

5. A method according to claim 1, wherein more than 500 parts by weight of said inorganic salt is added per 100 parts by weight of said elastomer material.

* * * * *